United States Patent [19]

Prasad

[11] Patent Number: 4,539,177
[45] Date of Patent: Sep. 3, 1985

[54] DENTAL ALLOYS FOR PORCELAIN-FUSED-TO-METAL RESTORATIONS

[75] Inventor: Arun Prasad, Cheshire, Conn.

[73] Assignee: Jeneric Industries, Inc., Wallingford, Conn.

[21] Appl. No.: 573,571

[22] Filed: Jan. 25, 1984

Related U.S. Application Data

[60] Division of Ser. No. 528,227, Aug. 31, 1983, , and a continuation-in-part of Ser. No. 400,481, Jul. 21, 1982, Pat. No. 4,419,325.

[51] Int. Cl.³ ................................................ C22C 5/04
[52] U.S. Cl. .................................. 420/463; 433/200.1
[58] Field of Search ............... 420/463, 464, 508, 580, 420/587; 433/200, 207, 222

[56] References Cited

U.S. PATENT DOCUMENTS 3,819,366  6/1974  Katz ..................................... 420/463
3,928,913 12/1975  Schaffer ............................. 420/463
3,989,515 11/1976  Reiff ................................... 420/464

Primary Examiner—Melvyn J. Andrews
Assistant Examiner—Deborah Yee
Attorney, Agent, or Firm—Barry Kramer

[57] ABSTRACT

A dental alloy for use in porcelain-fused-to-metal restorations including palladium, cobalt, gallium, gold, aluminum, copper, zinc and ruthenium or rhenium. The cobalt controls the coefficient of thermal expansion of the alloy to permit the use of the alloy with commercially available porcelains having a variety of thermal coefficients. The zinc serves as a scavenger during formation and casting of the alloy. The aluminum protects the alloy from absorbing gases during torch melting and during the porcelain firing process. The ruthenium or rhenium provides grain refining for the alloy to increase its elongation, tensile strength, and thus toughness. The alloy with ruthenium or rhenium as a grain refining agent must be made in a protective environment to avoid the formation of bubbles in the porcelain during the porcelain firing process.

8 Claims, 9 Drawing Figures

DENTAL ALLOYS FOR PORCELAIN-FUSED-TO-METAL RESTORATIONS

CROSS-REFERENCE TO RELATED APPLICATIONS

This application is a division of application Ser. No. 528,227 filed Aug. 31, 1983 which application was a continuation-in-part of application Ser. No. 400,481 filed July 21, 1982 now U.S. Pat. No. 4,419,325.

BACKGROUND OF THE INVENTION

This invention relates to palladium based dental alloys and, in particular, to alloys for use in porcelain-fused-to-metal restorations.

Porcelain-fused-to-metal restorations consist of a metallic sub-structure coated with a veneer of porcelain. Over the years various alloys have been proposed for the sub-structure of these restorations. Many of the early alloys used gold with some platinum or palladium as the main alloy ingredients. However, with the increases and fluctuations in the price of gold and platinum in recent years, other alloys have come to play major roles in this area. One series of alloys which has gained general acceptance is based on nickel, chromium and beryllium and the main ingredients. Another series of alloys, with which this invention is concerned, is based on palladium as the dominant element.

One such palladium based alloy for use in porcelain-fused-to-metal restorations is described in U.S. Pat. No. 4,261,744. This alloy includes approximately 80% palladium and lesser amounts of indium, tin, cobalt and silicon. Another palladium alloy, which was commercially available prior to this invention, includes, based on spectrographgic analysis, approximately 2% gold, 79% palladium, 9% gallium, 10% copper and perhaps a trace of boron (on the order of 0.1%). Alloys similar to this commercial alloy, which include gold, palladium, gallium, copper and boron are described in U.S. Pat. Nos. 3,134,671 and 4,179,288.

In examining the commercially available gold-palladium alloy described above, it was found that the alloy suffered a number of disadvantages in terms of its suitability for use in porcelain-fused-to-metal restorations. In particular, the alloy exhibited poor grain structure which gave it low elongation, lower than optimum tensile strength and low toughness, as well as making it susceptible to "hot-tearing" during the investment casting process.

Surprisingly, in seeking to overcome these limitations, numerous difficulties were encountered in attempting to grain refine this alloy. In particular, it was found that when the standard grain refining techniques were applied to the alloy, and the alloy then used to make a casting for a porcelain-fused-to-metal restoration, the casting caused bubbles to form in the porcelain during the porcelain firing process. This resulted in an unusable restoration.

Moreover it was found that the commercial gold-palladium alloy had a coefficient of thermal expansion which was not compatible with the full range of porcelains available for porcelain-fused-to-metal restorations. In particular, although the alloy could be used with porcelains having a low coefficient of thermal expansion, it could not be used with procelains having a high coefficient, particularly for long-span bridgework involving pontics.

Accordingly, it is one of the objects of this invention to overcome the limitations of the above described commercially available palladium based dental alloy. In particular, it is an object of this invention to provide a grain refined palladium based dental alloy which will not produce bubbles when porcelain is applied. It is a further object of the invention to produce a palladium based dental alloy which has a coefficient of expansion compatible with the complete range of dental porcelains commonly used in porcelain-fused-to-metal restorations.

The attainment of these and other objects of the invention is described below in connection with the description of the preferred embodiments of the invention.

SUMMARY OF THE INVENTION

In accordance with the invention, a palladium based dental alloy is provided which consists essentially of approximately 35–85% by weight palladium, 0–12% by weight copper, 5–15% by weight gallium, 0–50% by weight gold, 0–5% by weight aluminum, 0–13% cobalt, 0–0.5% zinc and 0.1–0.5% ruthenium, rhenium or mixtures thereof, the total of the constituents being 100%. Preferred embodiments of the alloy have approximate compositions by weight as follows:

| Pd | Cu | Ga | Au | Al | Co | Zn | Ru or Re |
|---|---|---|---|---|---|---|---|
| 78.7 | 10 | 9 | 2.0 | 0.1 | — | — | 0.2 |
| 78.7 | 7.5 | 9 | 2.0 | 0.1 | 2.5 | — | 0.2 |
| 80.7 | — | 9 | — | 0.1 | 10 | — | 0.2 |
| 78.6 | 10 | 9 | 2.0 | 0.1 | — | 0.1 | 0.2 |
| 78.6 | 7.5 | 9 | 2.0 | 0.1 | 2.5 | 0.1 | 0.2 |
| 80.6 | — | 9 | — | 0.1 | 10 | 0.1 | 0.2 |

The ruthenium or rhenium in these alloys serves as a grain refining agent. In accordance with the invention, to introduce these agents, the alloy must be made in a protective environment, such as, under vacuum or in a reducing or an inert atmosphere, e.g., at atmosphere of argon. If not done in this way, the alloy that is produced will contain absorbed gases which will cause bubbling of the porcelain during the porcelain firing process. Importantly, iridium, which is a known grain refining agent, is excluded from the invention because it fails to grain refine the alloy.

In copending application Ser. No. 400,481 it was shown that the use of a protective environment during the formation of the alloy and the incorporation of aluminum in amounts up to about 5% as part of the alloy essentially eliminate bubble formation during the porcelain firing process. For most conditions, a level of aluminum on the order of 0.1% has been found sufficient to eliminate bubbling. This is a desirable level for aluminum since it results in alloys which melt like precious alloys and generally leave a clean, i.e., metal-free, crucible when the molten alloy is cast. Under some conditions, however, e.g., overheating of the alloy during the casting process, the 0.1% level for aluminum has been found to be insufficient to eliminate completely bubble formation during the porcelain firing process. Although higher levels of aluminum can be used to guarantee bubble-free restorations, even for overheated alloys and the like, such higher levels result in an alloy which melts like a non-precious alloy and which leaves a film of metal and slag in ceramic crucibles. As a general proposition, dental laboratories prefer alloys whose melting characteristics are similar to gold, rather than to non-precious alloys. Also, the leaving behind of a film of metal represents a loss of material and thus is undesirable from an economic point of view.

It has now been found that bubble-free restorations can be achieved with low levels of aluminum through the inclusion of small amounts of zinc in the alloy. Such zinc-containing alloys melt like precious alloys and leave an essentially clean crucible. Moreover, these alloys have been found to produce finished restorations which are essentially bubble-free for a wide range of processing conditions.

BRIEF DESCRIPTION OF THE DRAWINGS

In FIG. 1, the coefficient of expansion of the alloy is greater than that of the porcelain so that the porcelain is under longitudinal compression in the final fused product, as is desired. In contrast, FIG. 2 illustrates the undesirable situation where the porcelain is under longitudinal tension in the final fused product because the coefficient of thermal expansion of the alloy is less than the coefficient of thermal expansion of the porcelain. The changes in length shown in these figures are for purposes of illustration only, and are not to scale.

DESCRIPTION OF THE PREFERRED EMBODIMENTS

Figure 1:
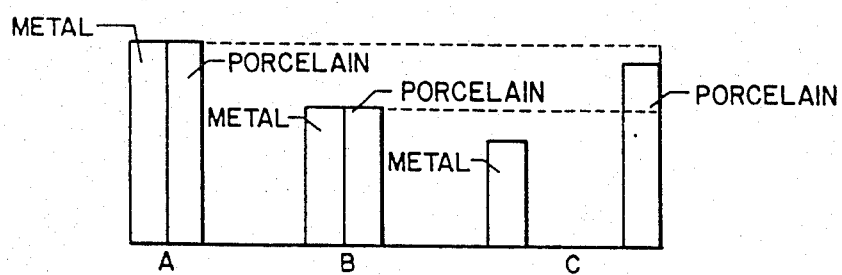
FIGS. 1 and 2 illustrate diagrammatically the importance of the relative coefficients of thermal expansion of the alloy and the porcelain.

The alloys of this invention can include the following constituents: gold, palladium, gallium, copper, aluminum, cobalt, zinc, ruthenium and rhenium.

Palladium and gold give the alloy its basic inertness so that it can withstand the environment of the patient's mouth. The relative amounts of these two components can be varied without changing the properties of the alloy. The palladium concentration of the alloy is preferably between about 35 and 85 wt. %, and most preferably between about 70 and 85 wt. %. The gold concentration is preferably between about 0 and 50 wt. %, and most preferably between about 0 and 10 wt. %.

Gallium and cobalt/copper reduce the melting point and strengthen the alloys. These components also form a protective and adherent oxide on the surface of the casting which reacts with the porcelain to produce a chemical bond. Of these elements, it was found that the combination of gallium and cobalt produces an oxide which is better for bonding porcelain than the oxide formed from the combination of gallium and copper.

The gallium concentration is preferably between about 5 and about 15 wt. %, and most preferably between about 6 and about 10 wt. %. The cobalt concentration is preferably between about 0 and 13 wt. %. The copper concentration is preferably between about 0 and 12 wt. %. When cobalt is used without copper, the cobalt range is most preferably from about 4 to about 10%. When copper is used without cobalt, the copper range is most preferably from about 5 to about 10%. If both copper and cobalt are used, the copper range is most preferably from about 5 to about 10%, and the cobalt range is most preferably from about 2 to about 6%.

As discussed in detail below, the cobalt serves to control the coefficient of thermal expansion of the alloy. The amount of this component is adjusted, for example, by substituting cobalt for copper, to provide coefficients of thermal expansion compatible with the complete range of porcelains available for porcelain-fused-to-metal restorations.

The aluminum serves to protect the alloy during torch melting and also during the porcelain firing process. Specifically, as the alloy is torch melted prior to being cast, the aluminum forms an oxide on the outside of the metal. This oxide substantially reduces the absorption of gases by the molten alloy. Such gases, if permitted to be absorbed, could later be released during the porcelain application process and thus form bubbles in the porcelain. Similarly, during the porcelain firing process, the aluminum forms a protective oxide when the metal substructure is heated.

Aluminum can be used in the alloy in amounts ranging up to about 5 wt. %. The preferred range for aluminum is between about 0.05 and 2 wt. %, with the most preferred concentration being approximately 0.1 wt. %. Higher amounts of aluminum can be used in place of gallium to lower the melting point and to strengthen the alloy.

The inclusion of zinc in the alloy serves to further reduce bubble formation during the porcelain firing process. The zinc functions as a scavenger during formation of the alloy and during the casting process. It has been found that small amounts of zinc, in combination with a protective environment and the use of aluminum, protect the alloy during manufacture, torch melting and the porcelain firing process, resulting in essentially complete elimination of bubbles in the finished restorations. Preferably between about 0.1 and 0.5 wt. % of zinc is included in the alloy, and most preferably between about 0.1 and 0.25 wt. %.

As discussed above, inclusion of zinc in the alloy allows for the use of lower levels of aluminum, e.g., on the order of about 0.1%, so as to produce an alloy which (1) melts like a precious alloy, (2) leaves a metal-free crucible during casting and (3) produces finished restorations which are essentially bubble-free for a wide range of processing conditions. The amount of zinc must be controlled in view of the presence of gallium in the alloy. In particular, zinc cannot be used in large quantities (e.g., more than 0.5% wt. %) with gallium because of the formation of a low melting phase along grain boundaries which make the alloy susceptible to tearing or fracture. Silicon, magnesium or mixtures thereof can be used to replace all or part of the zinc in the alloy. Of these three elements, zinc is considered the most preferred. When silicon is used in the alloy, its concentration is preferably kept below about 0.25%; when magnesium is used in the alloy, its concentration is preferably kept below about 0.50%.

Cobalt is used in the alloy to provide flexibility in the adjustment of the alloy's coefficient of thermal expansion. Gallium, copper and aluminum also affect the coefficient of thermal expansion, but to a much lesser extent. Flexibility in the ability to adjust the coefficient of thermal expansion is necessary in view of the broad range of porcelains available in the market.

Figure 2:
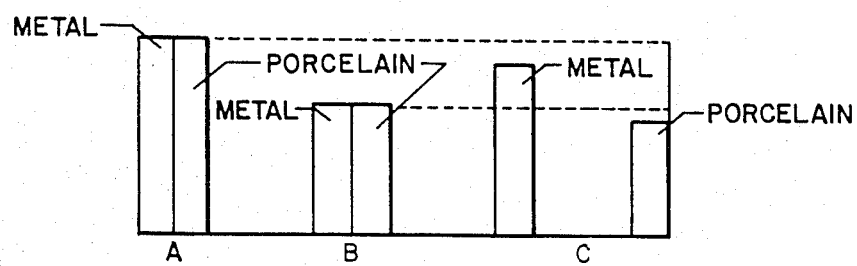

FIGS. 1 and 2 illustrate diagrammatically the effect on longitudinal contraction of different relative coefficients of thermal expansion for the porcelain and the alloy.

In FIG. 1, the metal is assumed to have a coefficient of expansion, and thus a coefficient of contraction, greater than that of the porcelain. Panel A of FIG. 1 shows the porcelain and alloy in their heated condition, just after the bond has formed between the porcelain and the oxides on the alloy. Panel B shows the porcelain and alloy, bonded together, in their cooled, contracted state. Panel C shows the contraction that would have occurred in the alloy and the porcelain if the two materials had not been bonded together.

Comparing panels B and C, we see that the metal component in panel C has a length shorter than the bonded porcelain-metal combination, while the porcelain component in panel C has a length greater than the bonded combination. Accordingly, for the bonded combination, the porcelain is under compression, because its length is less than the length it would have had if it had not been bonded to the alloy, while the alloy is under tension, because its length is greater than the length it would have had if it was not bonded to the porcelain.

FIG. 2 shows the identical set of conditions but for the coefficient of expansion of the metal being less than that of the porcelain. Again panel A shows the length of the alloy-porcelain combination in its heated condition. Panel B shows the length after cooling, and panel C shows the lengths the individual components would have had if they had not been bonded together. In this case, because the metal contracts less than the porcelain, the metal is under compression and the porcelain is under tension.

In terms of porcelain-fused-to-metal restorations, it is important that the porcelain be under compression, not tension. If it is under tension, cracks will form in the porcelain to relieve the tension. It is to achieve this condition of porcelain being under compression that varying amounts of cobalt are used in the alloy of the invention.

The following table illustrates the effect of varying the concentration of cobalt upon the thermal expansion of the alloy ($K_T$) at 500° C. The percentages shown in the first column of this table were determined using a Theta differential dilatometer, where the reference temperature was 30° C., the rate of temperature climb was 3° C./minute and the reference standard was pure platinum.

TABLE I

| Alloy | $K_T$ | Co | Cu | Pd | Ga | Al | Au | Ru |
|---|---|---|---|---|---|---|---|---|
| 1 | .670 | — | 10 | 78.7 | 9 | 0.1 | 2.0 | 0.2 |
| 2 | .685 | 2.5 | 7.5 | 78.7 | 9 | 0.1 | 2.0 | 0.2 |
| 3 | .725 | 10 | — | 78.7 | 9 | 0.1 | 2.0 | 0.2 |

Figure 3:
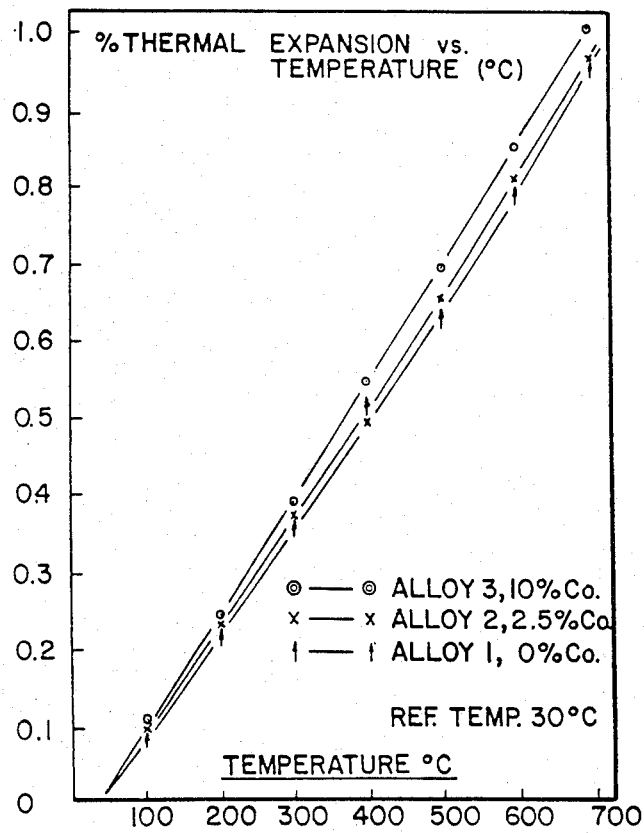
FIG. 3 is a plot of thermal expansion ($K_T$) versus temperature for three alloys having 10% cobalt (the upper curve), 2.5% cobalt (the middle curve) and no cobalt (the lower curve). The remainder of the composition of these alloys is given below in Table I.

FIG. 3 shows the behavior of $K_T$ over the range of temperatures from 30° C. to 700° C.

As can be seen from FIG. 3 and Table I, the substitution of cobalt for copper increases the amount of thermal expansion exhibited by the alloy which changes in temperature. This allows the production of alloys useful for a wide range of porcelains, in that, by adjusting the cobalt concentration, a thermal expansion for the alloy can be obtained which is greater than the thermal expansion of the porcelain so that, in the final restorations, the porcelain will be under compression. The thermal behavior of alloys including small amounts of zinc ranging up to about 0.5% are substantially the same as those described above for alloys without zinc.

The ruthenium or rhenium component of the alloy provides the important property of grain refining. Alloys consist of individual grains in contact with each other. The size of these grains is critical to the physical properties of the alloy. This size can vary from coarse to fine, and the grains can be regular or irregular.

Ideally, a dental alloy should have fine, regular grains. Alloys with this type of grain structure exhibit superior elongation, tensile strength and toughness properties. Moreover, such alloys are less prone to hot tearing during the investment casting process, as compared to alloys with a coarser grain structure. "Hot tearing", as understood in the art, involves the formation of cracks in the casting due to stresses produced in the casting as it cools in the investment. These cracks can result in failures which necessitate remaking the casting with the concomitant loss of the time, energy and material used to make the original casting.

In an attempt to improve the grain structure of the alloys of this invention ruthenium, rhenium and iridium were tested. Quite surprisingly, it was found that when these grain refiners were used, and the alloy was prepared in air, the conventional manufacturing technique for precious alloys, the resulting alloy was unsuitable for use in a porcelain-fused-to-metal restoration because it produced bubbles in the porcelain during the porcelain firing process. Only when the alloy was prepared in a protective environment, was a suitable alloy obtained. Moreover, when the grain refining element iridium was used, only poor grain refinement was achieved regardless of the particular method of preparation employed. This was found to be the case up to and including iridium concentrations as high as 0.5%.

Figure 4:
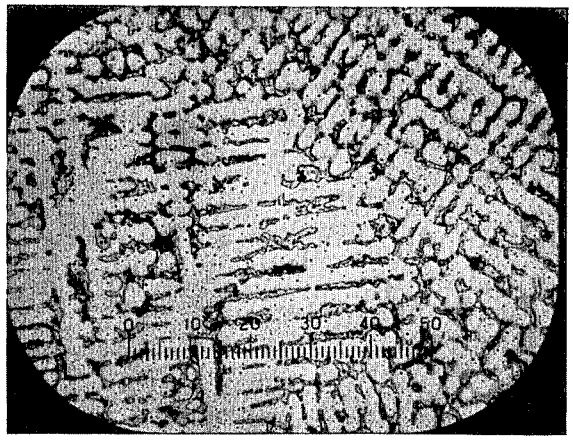
FIG. 4 is a photomicrograph showing the grain structure of the commercially availablee gold-palladium alloy discussed above.

FIGS. 4, 5, 6 and 7 show the effects of grain refining on the alloys of this invention. FIG. 4 is a photomicrograph of the grain structure of the commercially available gold-palladium alloy described above. As can be seen, the grain structure is coarse.

Figure 5:
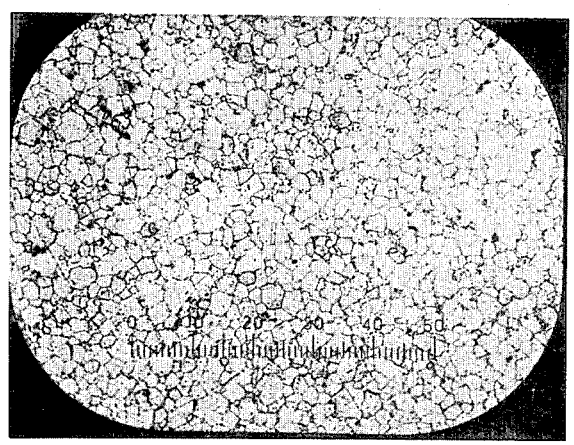
FIGS. 5 and 6 are photomicrographs showing the improved grain structure of the alloys of this invention when ruthenium (FIG. 5) or rhenium (FIG. 6) are used as grain refining agents.
Figure 6:
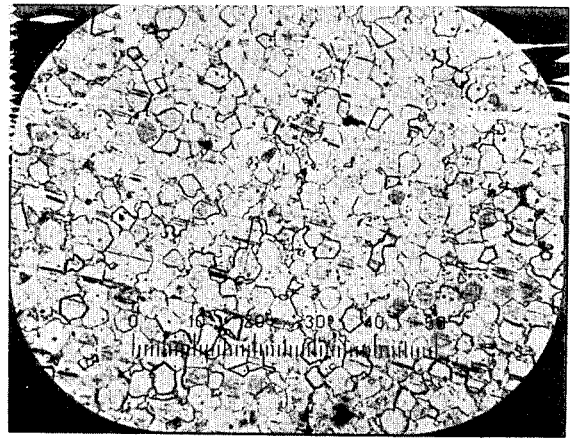

FIGS. 5 and 6 show the alloys of this invention where 0.2% by weight ruthenium or rhenium, respectively, have been added. The FIG. 5 alloy has the composition of alloy 1 in Table I; the FIG. 6 alloy has the same composition but with rhenium in place of ruthenium. As can be seen from these photomicrographs, the grain structure is now significantly improved in comparison to the commercially available alloy, and the alloy consists of regular, small grains. Essentially the same grain structure is achieved when the alloy includes small amounts of zinc.

Figure 7:
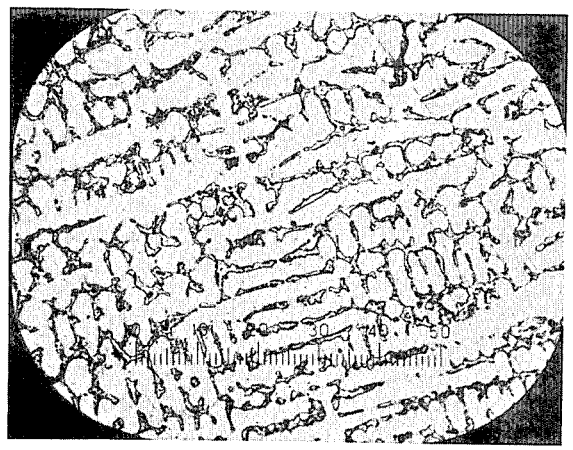
FIG. 7 is a photomicrograph showing the poor grain structure of the alloy when iridium is used as the grain refining agent.

FIG. 7 shows the situation when 0.2% iridium is used as a grain refiner. This alloy has the same composition as the alloys of FIGS. 5 and 6 but with iridium substituted for ruthenium or rhenium. Plainly, only very poor grain refining has been achieved and the grain of this alloy is more similar to that of the commercially available alloy (FIG. 4) than that achieved with ruthenium or rhenium (FIGS. 5 and 6). This poor grain structure still results even if the alloy includes zinc.

Table II shows the effect of grain refining on the physical characteristics of the alloy. Alloy A in this table has the composition of alloy 1 in Table I; alloy B has the same composition but with 0.2% more palladium and no ruthenium. As shown in the table, grain refining produces an alloy having increased strength, increased elongation and thus increased toughness. An Instron machine was used to measure the values reported. The same improved physical properties were observed when rhenium was used as the grain refining agent, but not when iridium was used. Also, the improved physical properties were found in the presence of zinc.

TABLE II

| Alloy | Yield Strength | Ultimate Tensile Strength | Elongation |
|---|---|---|---|
| A | 150,000 psi | 175,000 psi | 12% |
| B | 130,000 psi | 151,000 psi | 9% |

As mentioned above, the standard technique for forming a grain-refined alloy cannot be employed with the alloys of this invention because it leads to the formation of bubbles in the porcelain during the porcelain firing process. Rather, the grain-refined alloy must be formed in a protective environment, such as, under vacuum, in a reducing atmosphere or in an inert atmosphere, for example, an atmosphere of argon. Without proceeding in this way, the alloy absorbs gases from the atmosphere which are later released from the alloy during firing to form bubbles in the porcelain. Also, it has been found that carbon containing crucibles are not advantageous in the preparation of the alloys of the present invention. Rather, ceramic crucibles, e.g., zirconia crucibles, are preferred.

Figure 8:
FIG. 8 is a photograph of the porcelain surface produced when the grain-refined alloy is made in an inert atmosphere.
Figure 9:
FIG. 9 is a photograph of the porcelain surface produced when the grain-refined alloy is made in air.

FIGS. 8 and 9 illustrate the difference between forming the alloy in air and under the conditions of this invention. In each case, the alloy has the composition of alloy 1 in Table I.

FIG. 8 shows the surface of the porcelain when the elements making up the alloy including the grain refining agent are combined under a blanket of an inert gas, such as argon. The argon is preferably introduced after vacuum has been applied to the melting chamber to remove ambient air. Alternatively, a stream of argon can be passed through the chamber without first drawing a vaccum. As can be seen in FIG. 8, the procelain is smooth and bubble free. The same smooth porcelain surface also is achieved when the constituents are combined in a reducing atmosphere or under vacuum. When only a vacuum is used, the temperature of the melt and the applied vacuum must be controlled in view of the vapor pressures of the components of the alloy to avoid excessive relative losses of the more volatile components. In particular, when zinc is included in the alloy, a protective environment comprising a reducing or an inert gas, rather than a vacuum environment, should be used in forming the alloy in view of the relatively high vapor pressure of zinc.

In comparison to the smooth surface achieved when the alloy is made in a protective environment, FIG. 9 illustrates what happens to the porcelain if the grain-refined alloy is made in air. Plainly, porcelain with bubbles such as those shown in FIG. 9 would not be acceptable.

In addition to the requirement that the grain refined alloy be made in a protective environment, the grain refining agent must be introduced within a specific range of concentrations. In particular, at least 0.1% of grain refining agent must be added to achieve the improved physical properties and additions above about 0.5% tend to embrittle the alloy, as well as hardening it to the point where it cannot be rolled without first being annealed. The preferred range for the grain refining agent is between approximately 0.1 and 0.3 wt. %, the most preferred concentration being about 0.2 wt. %.

It should be noted that the improved grain and physical properties described above result whether the alloy is made in air or in a protective environment; it is only so that porcelain can later be applied to a casting made from the alloy that a protective environment has to be used in preparing the alloy. Also, the poor grain structure and physical properties described above for iridium result irrespective of whether the alloy is made in air, in vacuum or under an inert or reducing atmosphere.

Although specific embodiments of the invention have been described and illustrated, it is to be understood that modifications can be made without departing from the invention's spirit and scope. Thus the concentrations of palladium, gold, gallium, copper, aluminum, zinc, cobalt and ruthenium or rhenium can be varied from the percentages illustrated and alloys having the superior characteristics of the invention will still result. For example, the palladium concentration can be varied at least between 35 and 85% by weight; the copper concentration between 0 and 12%, the gallium concentration between 5 and 15%, the gold concentration between 0 and 50%; the aluminum concentration between 0 and 5%; the cobalt concentration between 0–13%; the zinc concentration between 0 and 0.5%; and the ruthenium or rhenium concentration between 0.1% and 0.5%.

I claim:

1. A method for reducing bubble formation during the firing of porcelain onto cast grain-refined palladium based dental alloys comprising:
   (a) initially forming a grain-refined palladium based molten alloy in a ceramic crucible in a protective environment;
   (b) admixing at least one oxide-forming element with said molten alloy to protect the alloy from absorbing gases during initial formation of the alloy, torch melting and casting, and the procelain firing process; and
   (c) admixing zinc with said molten alloy in an amount sufficient to serve as a scavenger during initial formation of the alloy, torch melting and casting, and the porcelain firing process; and
   (d) pouring said molten alloy into a mold and allowing said alloy to solidify therein in said protective environment.

2. The method of claim 1 wherein the protective environment comprises an atmosphere of an inert gas.

3. The method of claim 2 wherein the protective environment includes argon.

4. The method of claim 1 wherein the ceramic crucible is a zirconia crucible.

5. The method of claim 1 wherein the oxide-forming element is aluminum.

6. The method of claim 5 wherein the concentration of aluminum is between about 0.05 and 2.0 percent by weight and the concentration of zinc is between about 0.1 and about 0.5 percent by weight.

7. The method of claim 6 wherein the concentration of aluminum is about 0.1 percent by weight and the concentration of zinc is between about 0.1 and about 0.25 percent by weight.

8. The method of claim 1 wherein all or part of the zinc is replaced by silicon, magnesium or mixtures thereof.

* * * * *